US008553835B2

(12) United States Patent
Hangartner et al.

(10) Patent No.: US 8,553,835 B2
(45) Date of Patent: Oct. 8, 2013

(54) COMPUTED TOMOGRAPHY SCANNERS, X-RAY FILTERS AND METHODS THEREOF

(75) Inventors: Thomas N. Hangartner, Dayton, OH (US); Sangeetha Alladi, Beavercreek, OH (US)

(73) Assignee: Wright State University, Dayton, OH (US)

( * ) Notice: Subject to any disclaimer, the term of this patent is extended or adjusted under 35 U.S.C. 154(b) by 266 days.

(21) Appl. No.: 12/999,657

(22) PCT Filed: Jun. 18, 2009

(86) PCT No.: PCT/US2009/047797
§ 371 (c)(1),
(2), (4) Date: Apr. 6, 2011

(87) PCT Pub. No.: WO2009/155418
PCT Pub. Date: Dec. 23, 2009

(65) Prior Publication Data
US 2011/0261926 A1 Oct. 27, 2011

Related U.S. Application Data

(60) Provisional application No. 61/073,541, filed on Jun. 18, 2008.

(51) Int. Cl.
*A61B 6/03* (2006.01)
*G21K 3/00* (2006.01)
(52) U.S. Cl.
USPC ............................................ 378/19; 378/157
(58) Field of Classification Search
USPC .......................................... 378/157, 158, 19
See application file for complete search history.

(56) References Cited

U.S. PATENT DOCUMENTS

| | | | | |
|---|---|---|---|---|
| 6,173,039 | B1 * | 1/2001 | Hampel et al. | 378/150 |
| 2002/0037067 | A1 * | 3/2002 | Horiuchi | 378/4 |
| 2003/0058994 | A1 * | 3/2003 | Sembritzki | 378/108 |
| 2006/0159220 | A1 * | 7/2006 | Heuscher | 378/9 |

OTHER PUBLICATIONS

Feldkamp, et al., "Practical Cone-Beam Algorithm", J.Opt.Soc.Am, 1984, pp. 612-619.
Chen, "An Alternative Derivation of Katsevich's Cone-Beam Reconstruction Formula", Med. Phys. 30 (12), Dec. 2003, pp. 3217-3226.

(Continued)

*Primary Examiner* — Hoon Song
*Assistant Examiner* — Danielle Fox
(74) *Attorney, Agent, or Firm* — Dinsmore & Shohl LLP (57) ABSTRACT

A computed tomography scanner may include a component mounting assembly, an x-ray tube, a filter assembly, and a detector assembly. The filter assembly filters an x-ray fan or cone beam generated by the x-ray tube such that the x-ray beam comprises a high dose portion and one or more low dose portions. The filter assembly reduces the photon count of the low dose portions. The x-ray tube may be coupled to the component mounting assembly at a first end and the detector assembly coupled at a second end that is opposite from the first end. The component mounting assembly is rotatable about a rotation axis. The detector assembly includes an array of individual detector elements capable of detecting x-ray photons of the x-ray beam. The high dose portion strikes a high resolution region of the detector assembly and the low dose portion strikes a low resolution region of the detector assembly.

17 Claims, 8 Drawing Sheets

(56) References Cited

OTHER PUBLICATIONS

Noo, et al., "Image Reconstruction From Fan-Beam Projections on Less Than a Short Scan", Phys. Med. Bio. 47, 2002, pp. 2525-2546.
Zou, et al., "Image Reconstruction on PI-Lines by Use of Filtered Backprojection in Helical Cone-Beam CT", Phys. Med. Biol. 49, 2004, pp. 2717-2731.
David, et al., "Noninvasive In Vivo Monitoring of Bone Architecture Alterations in Hindlimb-Unloaded Female Rats Using Novel Three-Dimensional Microcomputed Tomography", Journal of Bone and Mineral Research, 2003, pp. 1622-1631.
Hangartner, "A Variable-Resolution Rotate-Only Computed Tomography Scanner", Med. Phys. 21, Oct. 1994, pp. 1557-1563.
Laib, et al., "Local X-Ray Tomography for In Vivo Bone Structure Examinations", Med. Phys. 26, Mar. 1999, pp. 447-452.
Laib, et al., "The Temporal Changes of Trabecular Architecture in Ovariectomized Rats Assessed by MicroCT", Osteoporosis International, 2001, pp. 936-941.
Neff, et al., "Quantified 2- and 3-Dimensional Evaluation of Bone Structures in Vitro and in Vivo", Osteologie 2002 (11) 2, pp. 67-77 (German language only)—Abstract in English, p. 1.
International Search Report, Application No. PCT/US2009047797 filed Jun. 18, 2009, completion of ISR is Jan. 25, 2010, pp. 1-10.

* cited by examiner

COMPUTED TOMOGRAPHY SCANNERS, X-RAY FILTERS AND METHODS THEREOF

TECHNICAL FIELD

Embodiments relate generally to computed tomography scanners and, more particularly, to computed tomography scanners and x-ray filters capable of providing focused high resolution imaging of internal structures.

BACKGROUND

Computed tomography is an imaging method employing tomography. In computed tomography, digital processing is used to generate a cross-sectional image of the inside of an object from a series of two-dimensional x-ray projection images taken around a single axis of rotation. A three-dimensional image can be created by stacking adjacent cross-sectional images or by directly generating an image from a series of two-dimensional x-ray projection images.

Helical (or spiral) cone beam computed tomography is a type of three dimensional computed tomography in which the source (usually of x-rays) describes a helical trajectory relative to the object while a two dimensional array of detectors measures the transmitted radiation on part of a cone of rays emanating from the source. In helical cone beam x-ray computed tomography scanners, the source and array of detectors move on a rotating gantry while the patient is moved axially at a uniform rate. Earlier x-ray computed tomography scanners imaged one slice at a time by rotating the source and a one-dimensional array of detectors while the patient remained static. The helical scan method reduces the measurement time for a given resolution. This is achieved, however, at the cost of greater mathematical complexity in the reconstruction of the image from the measurements.

Computed tomography produces a volume of data which can be manipulated, through a process known as windowing, in order to demonstrate various structures based on their ability to block the x-ray beam. Although historically the images generated were in the axial or transverse plane (orthogonal to the long axis of the body), modern scanners allow this volume of data to be reformatted in various planes or even as volumetric (3D) representations of structures.

In some applications, it is desired to generate images of small structures within a larger object. For example, the visualization of changes in small trabecular structures, required to understand bone physiology, requires the acquisition of complete images at high resolution. Trabecular structures range in size from 25 to 200 μm. However, such visualization presently requires exposure of the patient to increased doses of radiation. Therefore, because of such increased radiation requirements, high-resolution images of trabecular structures using computed tomography has been limited mostly to in-vitro analysis of bone biopsies.

Accordingly, the need still exists in the art for a focused high-resolution computed tomography scanner and method of scanning that reduces the radiation dose while maintaining the high resolution needed to image small structures.

SUMMARY

In one embodiment, a computed tomography scanner may include a component mounting assembly, an x-ray tube, a filter assembly, and a detector assembly. The x-ray tube radiates x-ray photons within an x-ray beam toward the detector assembly. The filter assembly is positioned in a path of the x-ray and includes an x-ray filter configured to pass x-ray photons propagating toward the detector assembly within a high dose portion of the x-ray beam. The filter is further configured to reduce a number of x-ray photons of the x-ray beam propagating toward the detector assembly in one or more low dose portions of the x-ray beam. The x-ray tube may be coupled to the component mounting assembly at a first end and the detector assembly coupled at a second end that is opposite from the first end. The component mounting assembly defines a central opening and is rotatable such that the x-ray tube and the detector assembly are rotatable about a rotation axis within the central opening. The detector assembly has an array of individual detector elements capable of detecting x-ray photons of the x-ray beam striking the detector element. The array of individual detector elements is configured such that the high dose portion of the x-ray beam strikes a high resolution region of the detector assembly and the one or more low dose portions strike one or more low resolution regions of the detector assembly.

In another embodiment, an x-ray filter assembly for use in a computed tomography scanner may include an x-ray filter and an x-ray shield component. The x-ray shield component may be made of an x-ray absorbing material that defines an opening through which a plurality of x-ray photons may pass. The opening of the x-ray shield component shapes an x-ray fan or cone beam comprising x-ray photons that pass through the opening. The x-ray shield is positioned before or after the x-ray filter component along the x-ray path and defines a filter opening. The x-ray filter is configured to allow x-ray photons propagating toward a detector assembly to pass through the filter opening to form a high dose portion of the x-ray beam and reduce a number of x-ray photons propagating toward the detector assembly through the filter portion to form one or more low dose portions of the x-ray beam.

In another embodiment, a method of generating a computed tomography image of an object is provided. The method includes generating an x-ray beam comprising a plurality of x-ray photons with an x-ray tube. The x-ray beam is filtered such that the x-ray beam includes at least one high dose portion and at least one low dose portion. The high dose portion propagates toward a detector assembly and passes through a high interest region within the object. The low dose portion has a reduced number of x-ray photons propagating toward the detector assembly and passes through a low interest region within the object. The method further includes rotating the x-ray tube and the detector assembly about the object. The x-ray photons of the high dose portion of the x-ray cone am are detected in a high resolution region of the detector assembly, and x-ray photons of the low dose portion of the x-ray beam are detected in a low resolution region of the detector assembly. The detected x-ray photons of the detector assembly are used to construct the computed tomography image.

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

Embodiments of the present disclosure relate to computed tomography scanners utilizing a filter assembly to yield high-resolution images of a small region of interest with the use of relatively low radiation doses. Radiation doses may be reduced by collecting data for only a small volume of interest with high precision and resolution and the remaining object at lower precision and resolution. As an example and not a limitation, embodiments of the present disclosure may be used to obtain high resolution images of a trabecular structure within a patient's bone (e.g., the radius or ulna of the forearm) to determine the bone status of the patient with relatively low radiation dosage.

In one embodiment, an x-ray tube producing an x-ray beam and a detector assembly cooperate to generate a computed tomography image of an object. The x-ray beam may be configured as a two dimensional x-ray fan beam to generate a single "slice" of the object, or a three dimensional x-ray cone beam to generate multiple "slices" of the object. The x-ray tube and detector assembly are rotated about the object to collect the data needed to reconstruct the image. A filter assembly is utilized to filter the x-ray beam such that the x-ray beam comprises a high dose portion that passes significantly through a high interest region of the object placed within the computed tomography scanner and one or more low dose portions that pass through the remaining regions of the object. The detector assembly comprises a two-dimensional array of detector elements in a high resolution region that measures the x-ray photons within the high dose portion and one or more low resolution regions that measure the x-ray photons within the low dose portion. The data provided by the array of detector elements may be used to generate one or more computed tomography images by image reconstruction algorithms. As explained in detail below, reducing the radiation dose in the low dose portions of the x-ray beam may also reduce the overall radiation dose experienced by the object being imaged.

Figure 1:
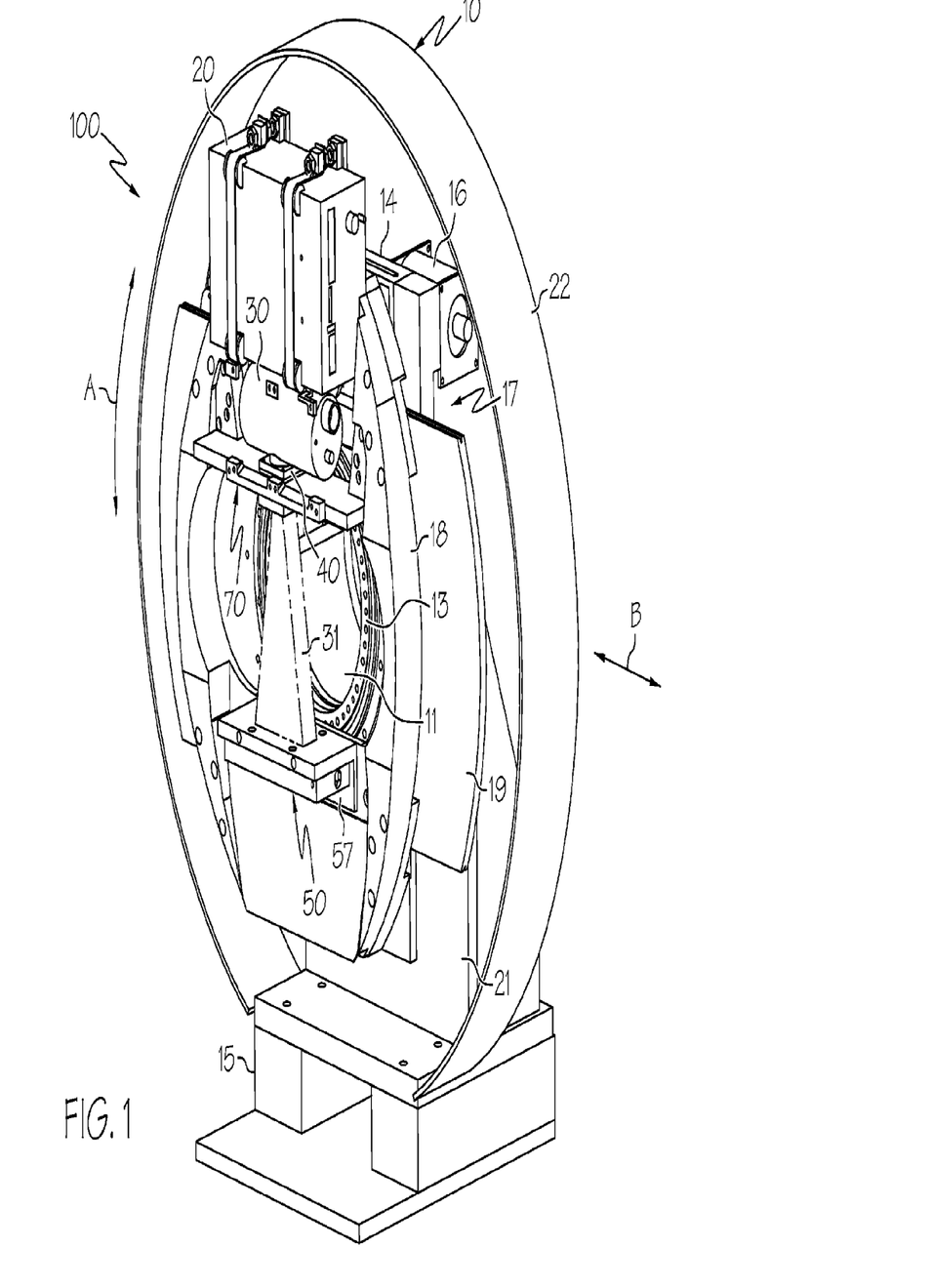
FIG. 1 depicts a diametric view of an exemplary computed tomography scanner according to one or more embodiments.

Referring to FIG. 1, an exemplary computed tomography scanner 100 is illustrated. It will be understood that computed tomography scanner configurations other than the configuration of the scanner illustrated in FIG. 1 may be utilized. The exemplary computed tomography scanner 100 comprises a gantry portion 10 and a base 15. The base 15 may support the gantry 10 and its related components, and may include a substantially vertical mounting pedestal 21. A component mounting assembly 17 is rotatably coupled to the mounting pedestal 21 via a ball bearing gear assembly 13. It will be understood that component mounting assembly 17 may be rotatably coupled to the mounting pedestal 21 via means other than the ball bearing gear assembly 13. The component mounting assembly 17 rotates as indicated by arrow A. In the illustrated embodiment, the component mounting assembly 17 comprises a rotating plate 19 and a translating plate 18. The rotating plate is coupled to the pedestal 21 via the ball bearing gear assembly 13.

Figure 2:
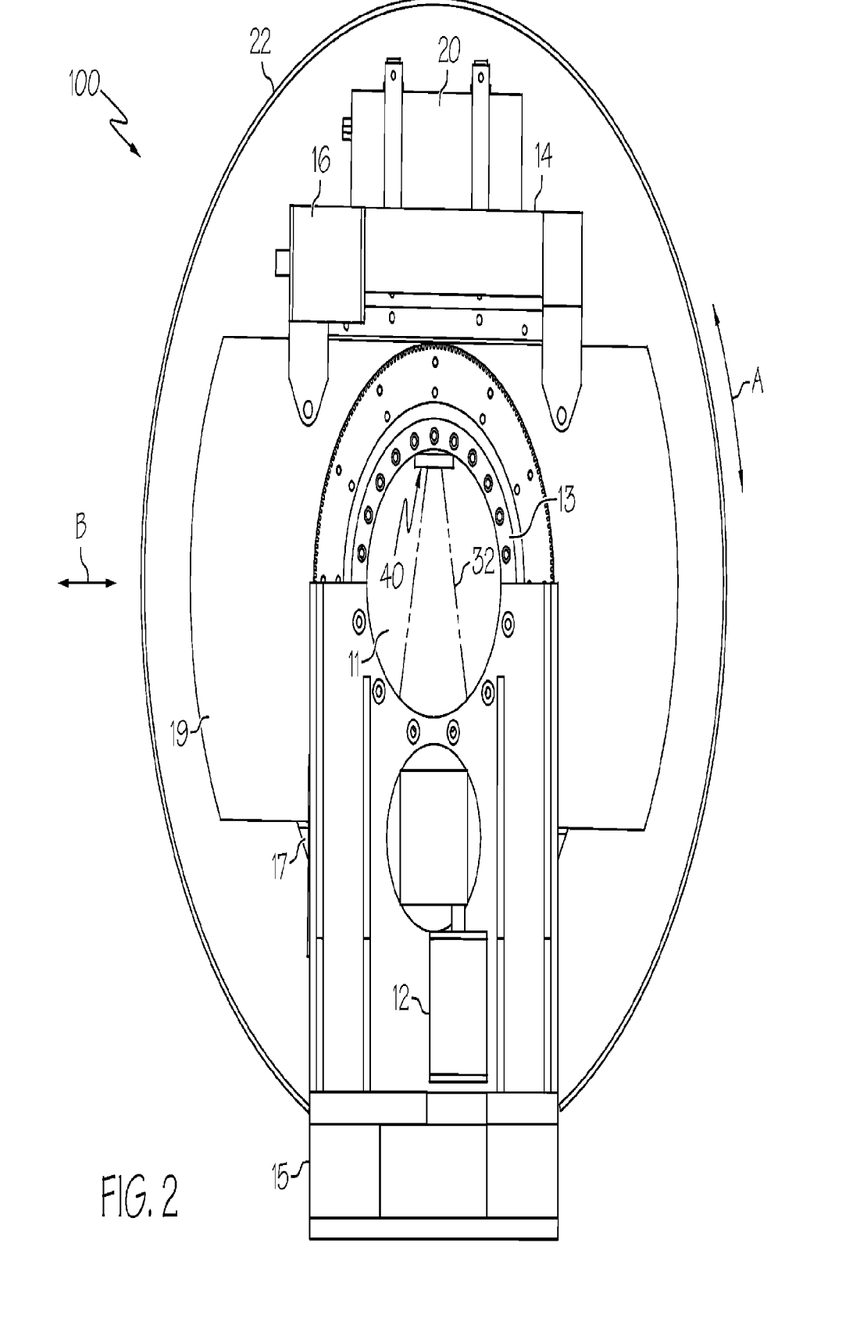
FIG. 2 depicts a rear view of an exemplary computed tomography scanner according to one or more embodiments.

Referring to both FIG. 1 and FIG. 2, a rotating motor 12 rotates the rotating plate 19 around the ball bearing gear assembly 13. The translating plate 18 is coupled to the rotating plate 19 via a lead screw assembly 14 and a servo motor 16. The lead screw assembly 14 and servo motor 16 allow the translating plate 18 and its associated components to move laterally along the axis indicated by arrow B. The axis indicated by arrow B will also rotate as the rotating plate 19 rotates. In some embodiments, the component mounting assembly 17 may only include a rotating plate 19 and, therefore, may only rotate and not translate. The pedestal 21, ball bearing gear assembly 13, rotating plate 19 and translating plate 18 define a central opening 11 through which the axis of rotation of the rotating plate 19 is located. Although the exemplary CT scanner is illustrated as a rotate-only cone-beam tomography system, other embodiments may incorporate means to longitudinally translate the object being scanned through the central opening 11.

As illustrated in FIG. 1, several components of the exemplary computed tomography scanner 100 are mechanically coupled to the translating plate 18. An x-ray tube source 30 is rigidly coupled to the translating plate 18 by any fastening means, such as screws, clamps, straps, etc. An x-ray power supply 20, filter assembly 40, filter bracket 70 and detector assembly 50 may also be mechanically coupled to the translating plate by any fastening means. The x-ray tube 30 is coupled to the translating plate 18 opposite from the detector assembly 50. In the illustrated embodiment, the x-ray tube 30 comprises a single x-ray tube source capable of generating an x-ray beam 31. Although FIG. 1 illustrates the x-ray beam 31 as an x-ray cone beam, other configurations of the x-ray beam 31 are also possible, such as an x-ray fan beam. The x-ray power supply 20 is mounted proximate the x-ray tube 30 and may be configured as a high-voltage power supply capable of providing power to the x-ray tube in accordance with a desired dosage of radiation. The filter assembly 40 is positioned in a path of the x-ray beam 31 generated by the x-ray tube 30 and may be coupled to the translating plate 18 by the filter assembly bracket 70. The detector assembly 50 may be coupled to the translating plate 18 by a detector assembly bracket 57.

The illustrated CT scanner further comprises a cable guide support 22 that supports cables that are used to electrically connect components within the gantry 10. The gantry 10 may also comprise a lead enclosure (not shown) that encloses the gantry 10 and the components maintained within to prevent x-ray radiation from escaping the gantry. The x-ray tube 30 and detector assembly 50 (and the other components connected to the translating plate 18) may rotate about an object positioned within the path of the x-ray beam 31. The x-ray photons of the x-ray beam 31 pass through the object toward the detector assembly 50, described in more detail below. In this manner, the x-ray beam 31 may scan the object from every desired angle.

Figure 3:
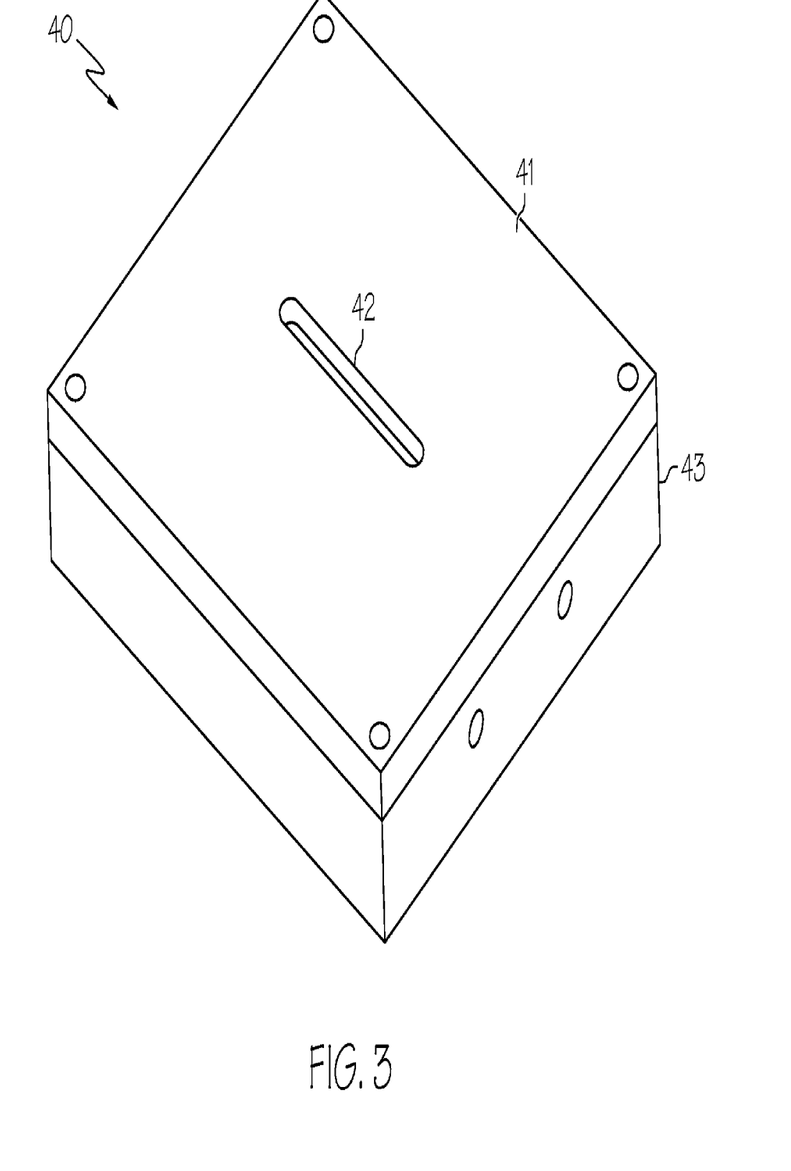
FIG. 3 depicts a perspective view of an exemplary filter assembly according to one or more embodiments.
Figure 4:
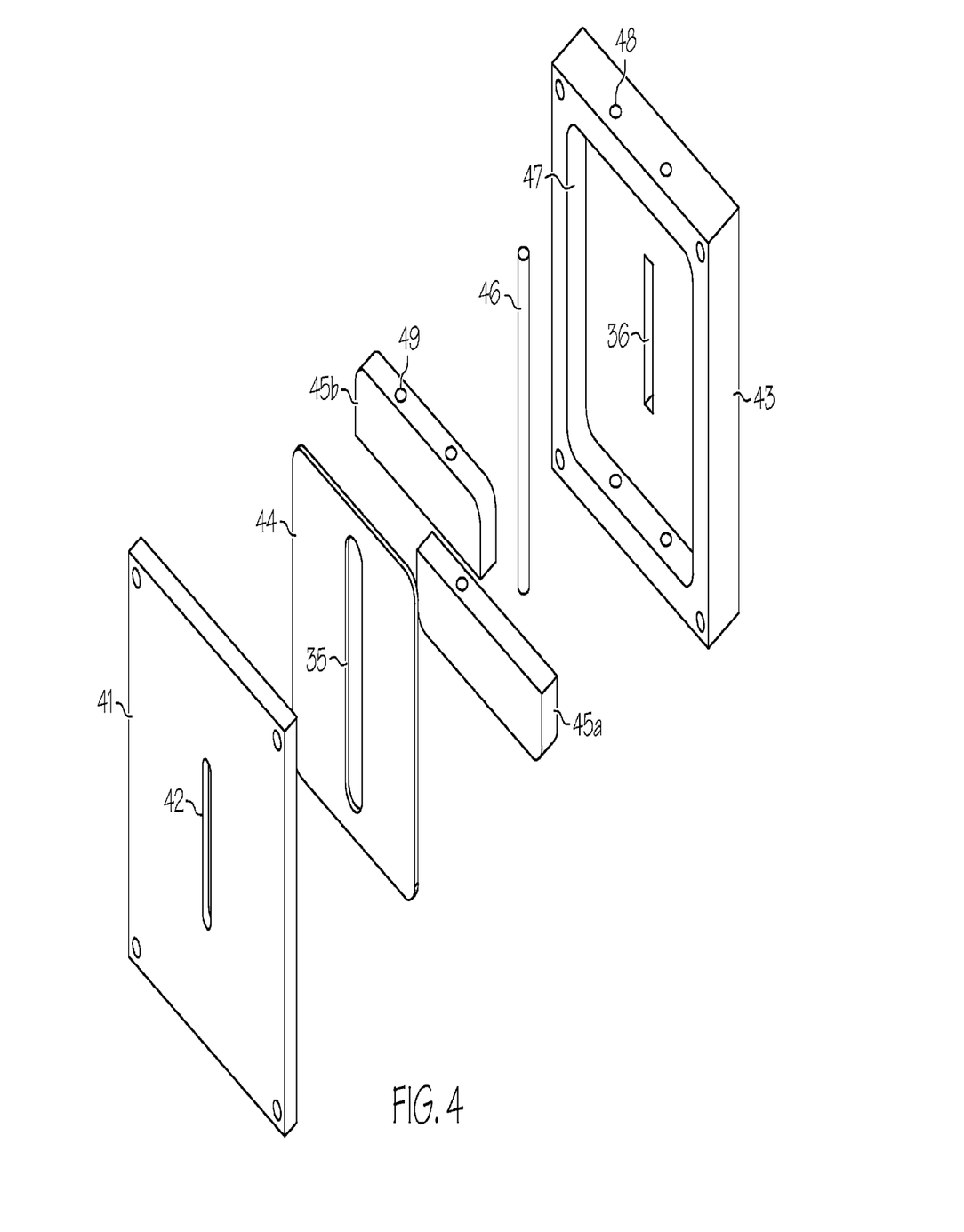
FIG. 4 depicts an exploded perspective view of an exemplary filter assembly according to one or more embodiments.

Referring now to FIGS. 3 and 4, an exemplary filter assembly 40 is illustrated. The illustrated filter assembly 40 comprises a filter enclosure 43 that defines a recess 47. The filter enclosure may be machined out of a material such as aluminum, for example. An enclosure opening 36 is provided in a bottom surface of the filter enclosure 47 to allow the x-ray beam 31 to pass through the filter assembly. A first and second filter element 45a and 45b that define a filter portion of the filter assembly 40 are maintained within the recess 47. The filter elements 45a and 45b are configured to reduce the number of x-ray photons reaching the detector assembly to form one or more low dose portions 32/33 of the cone beam 31 (see FIGS. 7 and 8). The type of material (e.g., copper, aluminum, etc.) and thickness of the filter elements 45a and 45b depend on the desired level of photon reduction. A filter opening defined by a distance between the first and second filter elements 45a and 45b is configured to allow substantially all x-ray photons to pass through, thereby forming a high dose portion 34 of the cone beam 31 (see FIGS. 7 and 8). Other filter configurations are also possible, such as a single filter component having a central opening through which x-rays may pass.

The positions of the first and second filter elements 45a and 45b may be adjustable such that the distance between the first and second filter elements 45a and 45b may be varied and the size of the high dose portion 34 of the x-ray beam 31 adjusted. For example, the filter enclosure 43 may include several adjustment holes 48 configured to accept filter adjustment rod 46. Filter elements 45a and 45b may be connected together via the adjustment rod 46 and holes 49. The adjustment rod 46 and the filter adjustment holes 49 are threaded such that a rotation of the adjustment rod 46 (e.g., via a screwdriver) changes the distance between the first filter element 45a and the second filter element 45b. Other adjustment means may also be utilized to adjust the size of the high dose portion 34 of the x-ray beam 31.

Positioned on top of the filter elements 45a and 45b within the recess 47 of the illustrated embodiment is an x-ray shield component 44. The x-ray shield component 44, which may be made of an x-ray absorbing and shielding material such as lead or tungsten, for example, is configured to absorb x-rays of the x-ray beam 31. The material of the x-ray shield component 44 defines an opening 35 that enables some x-rays to pass. The x-ray shield component 44 therefore defines the shape and size of the x-ray beam 31. The only x-ray beams that pass by the x-ray shield component 44 are those that pass through the opening 35. The filter assembly 40 further comprises a filter lid 41. The filter lid 41 is coupled to the filter enclosure 43 and comprises a corresponding opening 42 that is aligned with the opening 35 of the x-ray shield component 44 when the filter lid 41 is coupled to the filter enclosure 43.

Figure 5:
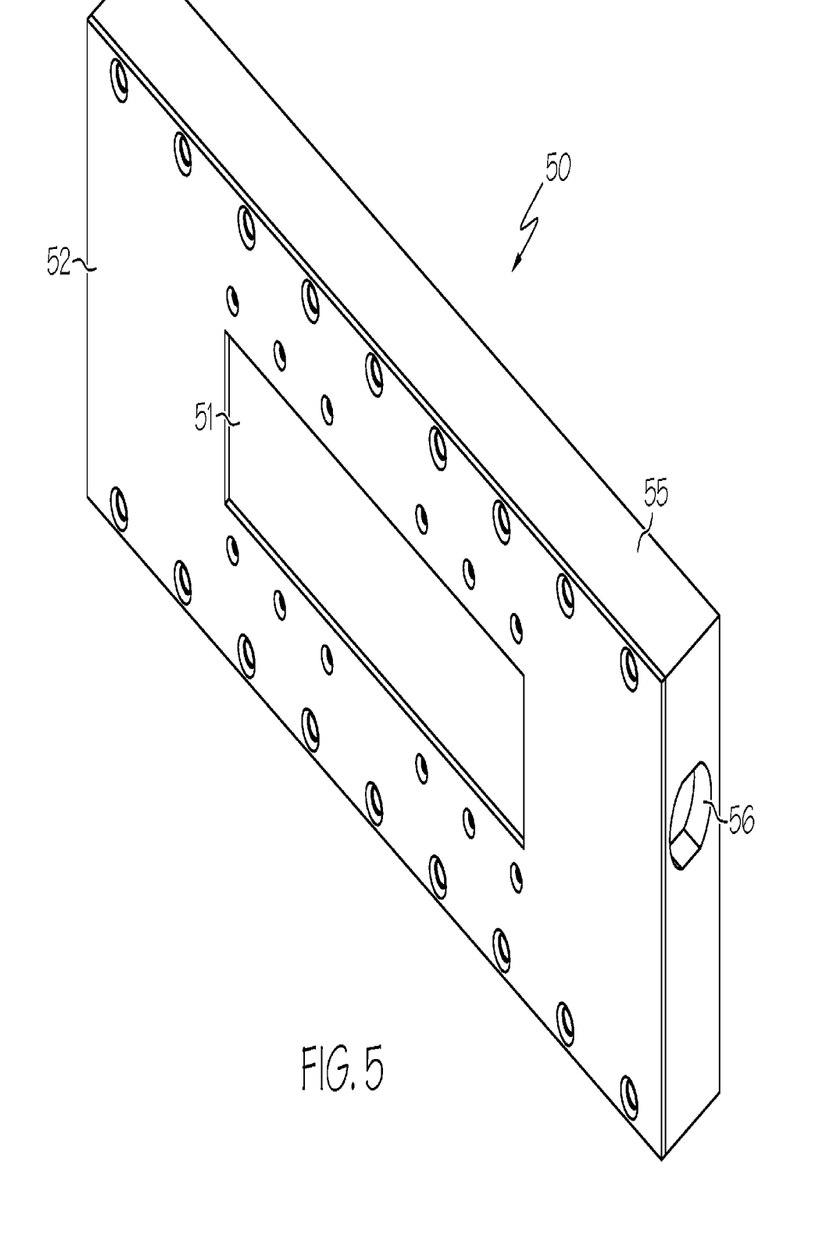
FIG. 5 depicts a perspective view of an exemplary detector assembly according to one or more embodiments.
Figure 6:
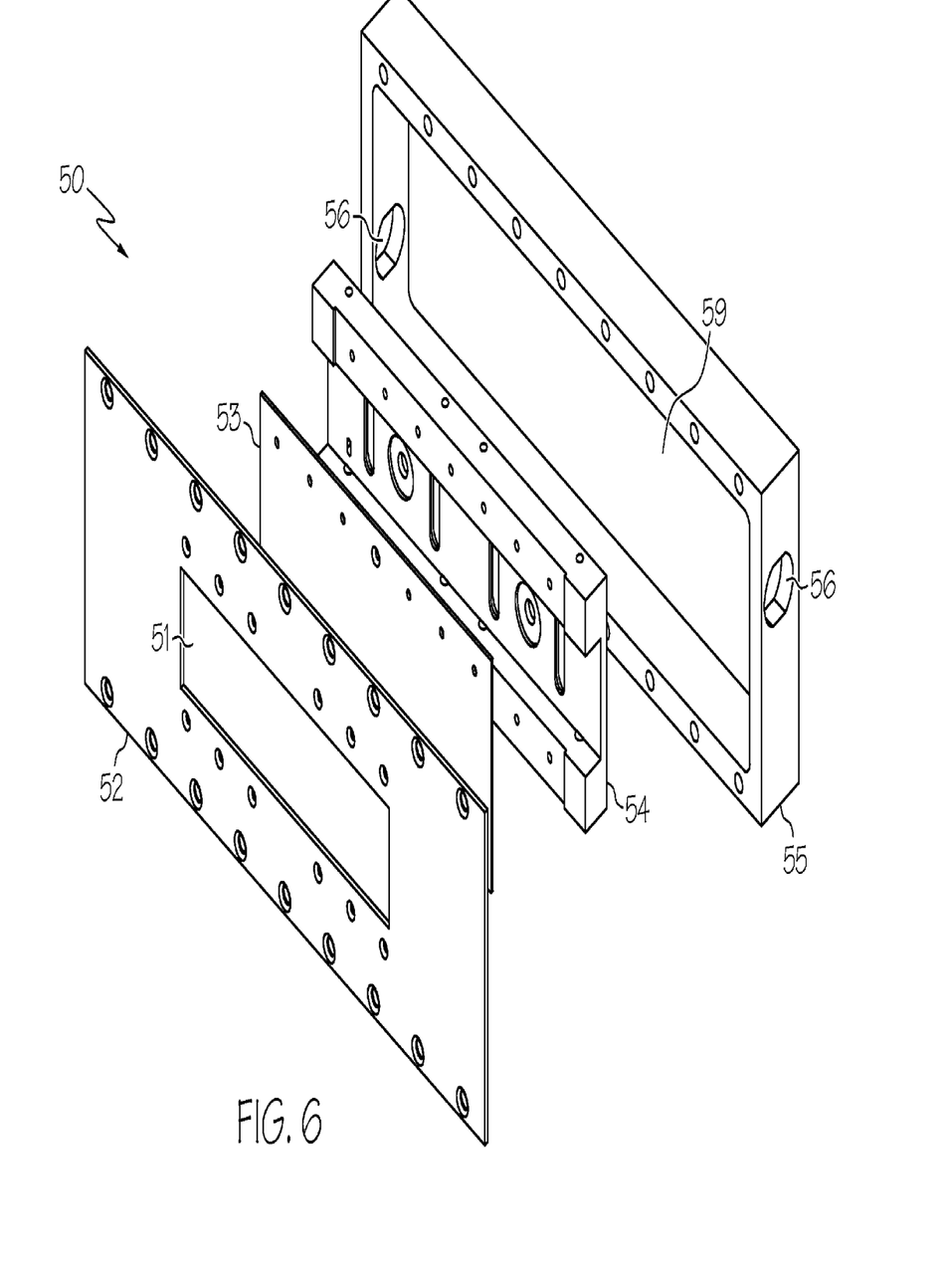
FIG. 6 depicts an exploded perspective view of an exemplary detector assembly according to one or more embodiments.

Referring now to FIGS. 5 and 6, an exemplary detector assembly 50 is illustrated. As described above, the detector assembly 50 may be attached to the translating plate 18 by the detector assembly bracket 57. The detector assembly 50 may comprise a detector assembly enclosure 55 that defines a detector enclosure recess 59. In the illustrated embodiment, the detector assembly enclosure 55 further comprises two holes 56 through which detector cables (not shown) may be routed. It will be understood that other cable routing configurations may be utilized. The detector assembly enclosure 55 may be made of a material such as aluminum. A detector holder 54, which may also be made of aluminum, for example, is configured to maintain the x-ray detector module (not shown) within the detector enclosure recess. The detector module may be a two dimensional x-ray detector array, comprising a two dimensional array of x-ray detector elements, or a one dimensional detector array, comprising a one dimensional array of x-ray detector elements. Exemplary detectors arrays include indirect detectors, consisting of a scintillator coupled to a CCD or similar light detector, and direct detectors, consisting of semiconductor flat panels that convert x-ray energy directly into electrical signals.

The individual detector elements are capable of providing a signal corresponding to the number of x-ray photons detected to a processor module such as a microcontroller, computer, or other similar hardware. As described below, the array of detector elements may comprise a high resolution region and one or more low resolution regions (see FIGS. 7 and 8). In one embodiment, a single detector may be used, and in other embodiments more than one detector may be used. The number of detector elements in the high-resolution portion of the two-dimensional detector array is determined by the size of the smallest structure to be visualized. The number of detector elements in the outer lower-resolution regions is determined by the desired cutback in spatial resolution, which results in reduced radiation dose. The reduction in resolution in the low resolution regions allows for the use of coarser detector elements. It is noted that the low-resolution region of the detector does not necessarily require a detector with lower resolution than the high-resolution region, but the low resolution region can be imaged with a high resolution detector if desired. As such, the phrase "low resolution region" refers to the resolution of measurement, not necessarily the resolution capabilities of the detector.

Coupled to a top surface of the detector holder 54 is a carbon sheet 53 that covers the detector array. The carbon sheet 53 is used to protect the detector surface and eliminate ambient light from reaching the detector without substantially inhibiting the x-ray photons from reaching the detector. In other embodiments, no carbon sheet 53 is utilized.

A detector assembly lid 52 may be connected to detector assembly enclosure 55 such that the carbon sheet 43, detector array, and detector holder 54 are enclosed by the detector assembly lid 52 and the detector assembly enclosure 55. The detector assembly lid 52 comprises a detector window 51 that allows x-rays within the x-ray beam 31 to reach the detector array through the carbon sheet. The components of the detector assembly 50 may be mechanically coupled together by any fastening means, such as by use of screws and the illustrated screw holes. The size and shape of the detector array, carbon sheet 53 and detector window may correspond with the size and shape of the x-ray beam 31 (see FIG. 1).

Figure 7:
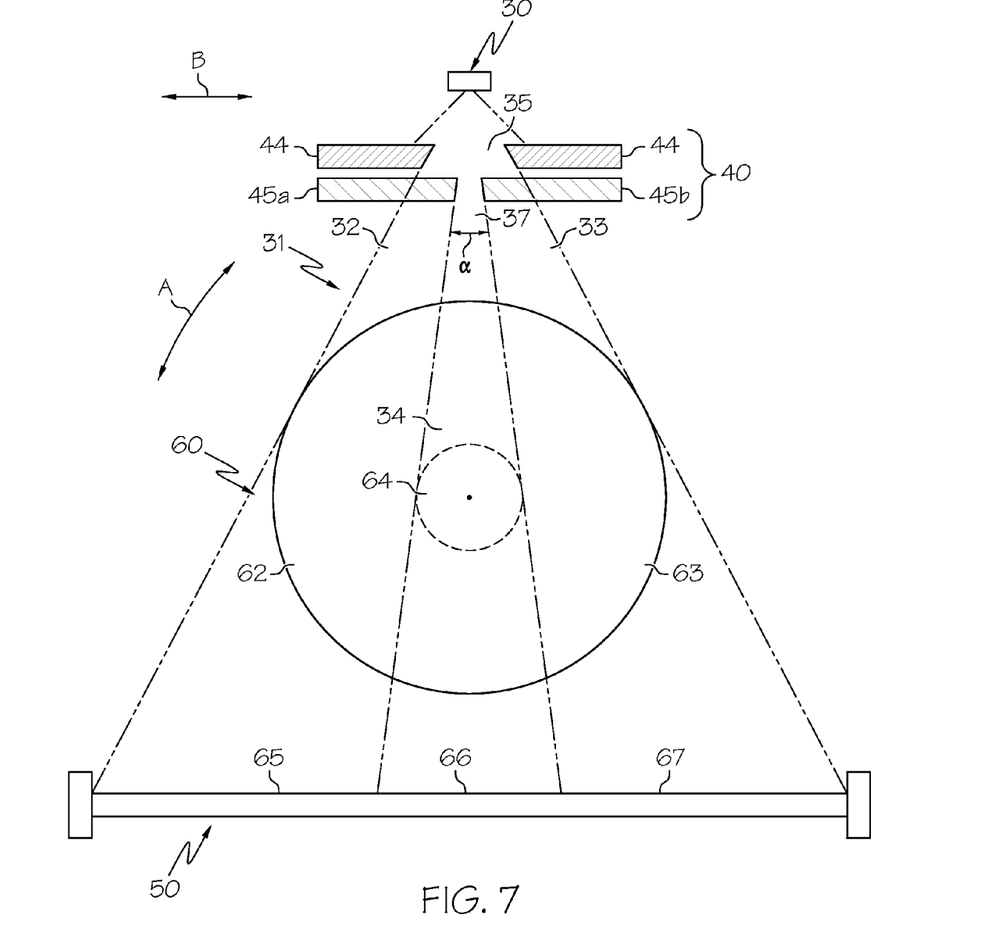
FIG. 7 depicts a schematic illustration of an exemplary x-ray beam, an exemplary filter assembly and an exemplary detector assembly according to one or more embodiments.

FIG. 7 is a schematic representation of one embodiment. An object 60 to be imaged is positioned within the path of the x-ray beam 31. In the illustrated embodiment, the object 60 is divided into three regions: a first low interest region 62, a high interest region 64 and a second low interest region 63. As described above, the x-ray tube 30 is configured to generate an x-ray beam 31. The filter assembly 40 is positioned within a path of the x-ray beam 31. The x-ray shield component 44 within the filter assembly 40 blocks a portion of the radiated cone beam 31. The portion of the x-ray beam 31 that passes through the opening 35 of the x-ray shield component 44 then reaches the first and second filter elements 45a and 45b. The x-ray beams that pass through filter elements 45a and 45b are attenuated and form low dose portions 32 and 33 of the x-ray beam 31, respectively. The x-rays passing through opening 37 between the first and second filter elements 45a and 45b are not attenuated and form the high dose portion 34 of the x-ray beam 31. The high dose portion 34 comprises a high dose fan angle $\alpha$ that is defined by the size of the opening 37. The high dose portion 34 passes substantially through the high interest region. The translating plate 18 may be moved along axis B to ensure that the high dose portion 34 passes through the high interest region 64 by use of an effective off-center rotation. In one embodiment, an initial coarse scan is performed by rotating the x-ray tube 30 and detector assembly 50 about the object to determine the location of the high interest region 64. After the location of the high interest region 64 is determined, the translating plate 18 may be moved concurrently as the rotating plate 19 is rotated during the high resolution scan.

The x-ray tube 30 and the detector assembly 50 are aligned such that the x-ray beam 31 strikes the detector assembly 50 after passing through the object 60. The high dose portion 34 of the x-ray beam 31 passes through the high interest region 64 and strikes a high resolution region 66 of the detector assembly 50, while the low dose portions 32 and 33 of the x-ray beam 31 pass through the low interest regions 62 and 63 and strike low resolution regions 65 and 67, respectively.

To reduce the radiation dose experienced by the object, there is a reduction factor in both resolution of the low resolution regions 65, 67 and photon counts of the low dose portions 32, 33 of the x-ray beam 31. The reduction in photon counts is achieved through the use of filter elements 45a and 45b, as described above. For example, the material selection and filter element thickness may be chosen such that the photon counts in the low dose portions 32, 33 of the x-ray beam 31 are reduced by a factor of six relative to the photon count in the high dose portion 34. In this case, the filter elements 45a and 45b are designed to pass ⅙ of the x-ray photons while absorbing the remainder. The reduction of resolution in the low resolution regions 65, 67 may be achieved by utilizing coarser detector elements in the detector array of the detector assembly 50. As an example, where a single detector element within the high resolution region 66 may be configured to detect a particular x-ray intensity, a factor of four reduction in the low resolution regions 65, 67 would dictate that four detector elements will be utilized to detect the same intensity. Therefore, in this example, the low resolution regions 65, 67 would have a resolution that is one fourth of the resolution of the high resolution region 66. Other factor values may be chosen for photon count and resolution depending on the desired dosage reduction and resolution requirements of the particular imaging application.

To obtain all of the data to reconstruct the computed tomography image, the x-ray tube 30, filter assembly 40 and detector assembly should be rotated about the object 60 by 180 degrees plus the fan angle α as indicated by arrow A. This ascertains that all projection angles needed for proper reconstruction of the image are measured at least once; however, some projection angles are measured twice.

The signals (i.e., projection data) provided by the detector elements of the detector assembly 50 may be collected and stored in a processor module (not shown) such as a computer or other similar hardware. A reconstruction algorithm may be applied to the projection data to create the computed tomography image. For example, a cone-beam filtered-back projection algorithm may be used to reconstruct images from the measured projection data. Because of the lower resolution in the low resolution regions 65, 67 of the detector array, interpolation of missing data in the outer low-resolution regions may be used to generate the data for convolution and back projection. Alternative reconstruction schemes may further reduce the need for data collection and reconstruction in the low resolution regions 65, 67 by allowing flexibility in terms of possible source trajectories. However, these algorithms may restrict the location of the high-resolution region of interest.

Computer simulations using filtered back projection indicate that complete elimination of projection data in the low interest regions 62, 63 does provide the highest reduction in dose, but it degrades the image quality in the high-resolution volume of interest, such that the image is rendered useless. However, other reconstruction algorithms that allow for truncation of data may eliminate the need for the low-resolution measurement while providing a high resolution image of the high interest region 64. In this case, only a high dose portion 34 may be generated and passed through only the high interest region 64 of the object, thereby eliminating the low dose portions 62 and 63 of the x-ray beam 31.

The dose was calculated for various reductions in photon count rate and spatial resolution for the regions outside of the high interest region (i.e., photon rate reduction in the low dose portions 32, 33 of the x-ray beam 31 and resolution reduction in the low resolution regions 65, 67 of the detector assembly 50). For a high-resolution region with a diameter that is 15% of the total object diameter, a complete cutback of the photon counts in the two low interest regions 32, 33 may result in a maximum achievable dose savings of 75%.

A savings of 37%-74% in dose was obtained using various reduction factors. For example, a factor two decrease in spatial resolution or photon counts in the low interest regions 62, 63 may result in a minimum savings of 37%. A factor six reduction in both spatial resolution and photon counts between the high interest region 64 and the low interest regions 62, 63 may result in a dose savings of 74% and leave the image information in the high-resolution central region intact. Additional cutbacks greater than a combined factor of thirty-six may result in significant changes in dose but may degrade the spatial resolution in the volume of interest.

Figure 8:
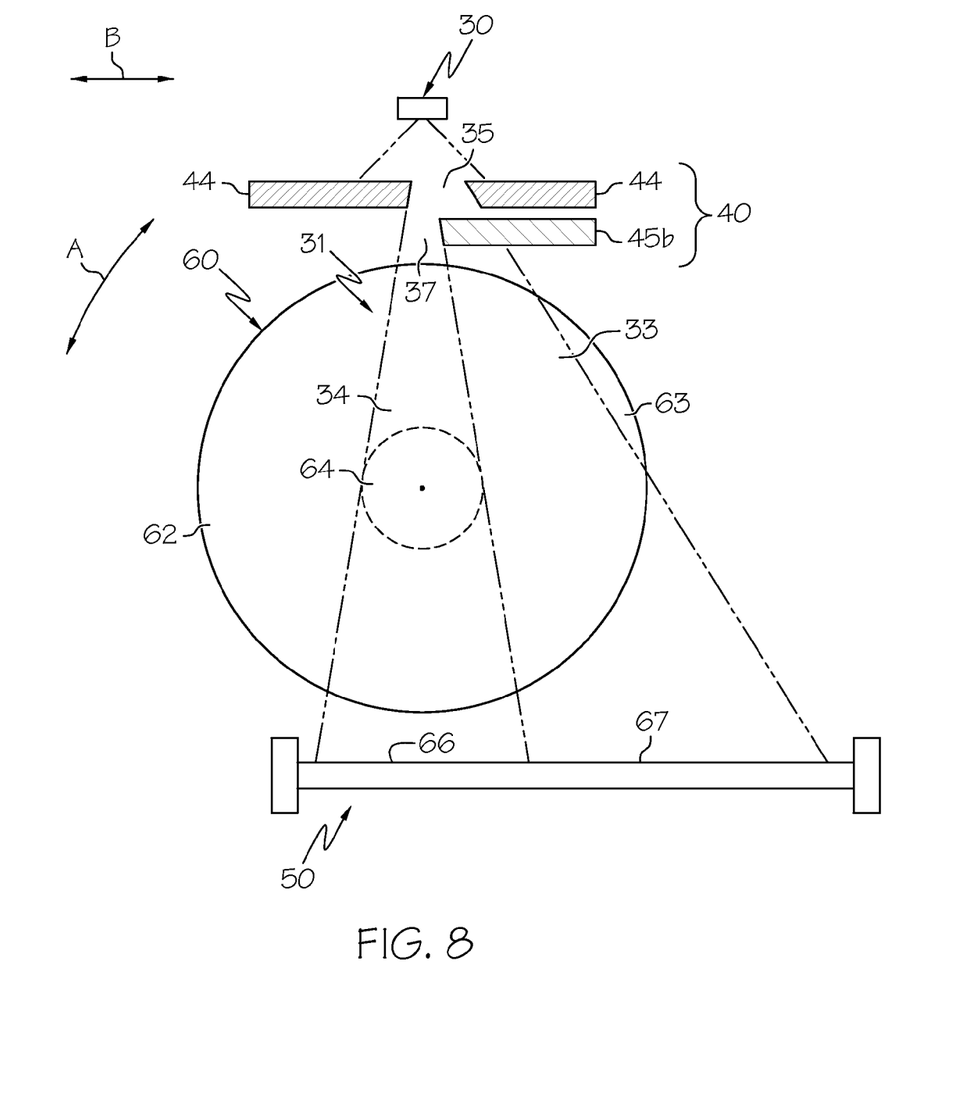
FIG. 8 depicts a schematic illustration of an exemplary x-ray beam, an exemplary filter assembly and an exemplary detector assembly according to one or more embodiments.

Referring now to FIG. 8, a schematic representation of another embodiment is illustrated. An object 60 to be imaged is positioned within the path of the x-ray beam 31. In the illustrated embodiment of FIG. 8, the x-ray tube 30 is configured to generate an x-ray beam 31. The filter assembly 40 is positioned within a path of the x-ray beam 31. The x-ray shield component 44 within the filter assembly 40 blocks a portion of the radiated x-ray beam 31. The filter assembly 40 comprises a single filter element 45b rather than two as illustrated in the embodiment of FIG. 7. The portion of the x-ray beam 31 that passes through the opening 35 of the x-ray shield component 44 will then reach the single filter element 45b. The x-ray photons that pass through filter element 45b are attenuated and form a single low dose portion 33 of x-ray beam 31. The x-rays passing through opening 35 that are not obstructed by the single filter element 45b form high dose portion 34 of the x-ray beam 31.

The high dose portion 34 passes substantially through the high interest region. The translating plate 18 may be moved along axis B to ensure that the high dose portion 34 passes through the high interest region 64 by use of an effective off-center rotation. As described above, an initial coarse scan may be performed by rotating the x-ray tube 30 and detector assembly 50 about the object 60 to determine the location of the high interest region 64. After the location of the high interest region 64 is determined, the translating plate 18 may be moved concurrently as the rotating plate 19 is rotated during the high resolution scan.

Initially, the single low dose portion 33 of the x-ray beam 31 passes through a portion of a low interest region 63 of the object 60. Because only one low dose portion 33 is present in the x-ray beam 31, the detector array of the detector assembly 50 may be relatively smaller than the detector array used in the embodiment illustrated in FIG. 7. As illustrated, the detector assembly 50 may be shifted such that the detector array comprises a high resolution region 66 configured to detect x-rays in the high dose portion 34 of the x-ray beam 31 and a low resolution region 67 configured to detect x-rays in the low dose portion 33 of the x-ray beam 31. In this embodiment, low interest region 62 of the object 60 does not initially receive a radiation dose. By rotating the x-ray tube 30, filter assembly 40 and detector assembly 50 by 360 degrees about the object, the low dose portion of the x-ray beam 31 passes through all of the low interest regions 62 and 63 and is measured at low resolution region 67. In this manner, data may be collected for all of the low interest region (i.e., regions 62 and 63) and the high interest region 64. Because the x-ray tube, filter assembly 40 and detector assembly 50 are rotated 360 degrees, the low interest regions 62 and 63 are measured only once compared to the high-resolution region 64, which is measured twice. Therefore, the dose for this embodiment may be reduced appropriately.

By using x-ray filters in conjunction with low resolution detector arrays, embodiments of the present disclosure may be used as a clinical research tool that permits low-dose, high-resolution imaging of small structures on the order of 50 µm and smaller. For example, this low-dose imaging enables in-vivo imaging of trabecular bone in both humans and small animals. This, in turn, will enable a greater understanding of physiological processes associated with bone under normal, disease, and treatment conditions. Low-dose imaging of structures at high-resolution may eliminate the need for invasive procedures associated with obtaining bone biopsies traditionally used in the study of certain anatomical properties of bone. This technique may simplify the performance of longitudinal studies needed for a better understanding of bone physiology under normal, disease, and treatment conditions. Embodiments may also permit low-dose imaging of non-biological objects such as foams, composites, castings etc.

For the purposes of describing and defining embodiments of the present disclosure, it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

It is noted that recitations herein of a component being "configured" or "operable" in a particular way, "configured" or "operable" to embody a particular property, or function in a particular manner, are structural recitations as opposed to recitations of intended use. More specifically, the references herein to the manner in which a component is "configured" or "operable" denotes an existing physical condition of the component and, as such, is to be taken as a definite recitation of the structural characteristics of the component.

It is also noted that recitations herein of "at least one" component, element, etc., should not be used to create an inference that the alternative use of the articles "a" or "an" should be limited to a single component, element, etc.

It is further noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A computed tomography scanner comprising a component mounting assembly, an x-ray tube, a filter assembly, and a detector assembly, wherein:
   the x-ray tube is operable to radiate x-ray photons within an x-ray beam toward the detector assembly;
   the x-ray tube is coupled to the component mounting assembly at a first end, and the detector assembly is couple to the component mounting assembly at a second end that is opposite from the first end;
   the component mounting assembly is rotatable such that the x-ray tube and the detector assembly are rotatable about a rotation axis within a central opening of the component mounting assembly;
   the filter assembly is positioned in a path of the x-ray beam and comprises an x-ray filter with a first filter element and a second filter element and configured to pass x-ray photons propagating toward the detector assembly within a high dose portion of the x-ray beam, and reduce the number of x-ray photons propagating toward the detector assembly in one or more low dose portions of the x-ray beam,
   a filter enclosure defining a recess, an x-ray shield component and a filter lid,
   the first and second filter elements are slidably positioned within the recess such that a size of the high dose portion of the x-ray beam is defined by a distance of the first filter element from the second filter element,
   the x-ray shield component is positioned within the recess, and comprises an x-ray absorbing material that defines an opening through which x-ray photons of the x-ray beam may pass toward the detector assembly, and
   the filter lid is coupled to the filter enclosure and comprises a corresponding opening that is aligned with the opening of the x-ray shield component when the filter lid is coupled to the filter enclosure; and
   the detector assembly comprises an array of detector elements capable of detecting x-ray photons of the x-ray beam, and configured such that the high dose portion of the x-ray beam strikes a high resolution region of the detector assembly and the one or more low dose portions of the x-ray beam strike one or more low resolution regions of the detector assembly.

2. A computed tomography scanner as claimed in claim 1 wherein a resolution of the high resolution region of the detector assembly is six times as great as a resolution of the low resolution region of the detector assembly, and the x-ray filter is configured such that a photon count in the high dose portion of the x-ray beam is six times as great as a photon count in the low dose portion of the x-ray beam.

3. A computed tomography scanner as claimed in claim 1 wherein the opening of the x-ray shield component is a slit operable to define a shape of the x-ray beam.

4. A computed tomography scanner as claimed in claim 1 wherein the x-ray filter is adjustable to increase and decrease a size of the high dose portion of the x-ray beam.

5. A computed tomography scanner as claimed in claim 1 wherein:
   the first filter element and the second filter element are positioned in a filter plane; and
   a position of the first filter element and a position of the second filter element is adjustable such that a size of the high dose portion of the x-ray beam is adjustable.

6. A computed tomography scanner as claimed in claim 1 wherein:
   the x-ray beam comprises a first low dose portion and a second low dose portion;
   the high dose portion of the x-ray beam comprises a high dose fan angle and is located between the first and second low dose portions;
   the high dose portion of the x-ray beam is configured to pass through a high interest region within an object, the first low dose portion of the x-ray beam is configured to pass through a first low interest region within the object, and the second low dose portion of the x-ray beam is configured to pass through a second low interest region within the object;

the detector assembly comprises a high resolution region, a first low resolution region, and a second low resolution region;

the detector assembly is positioned on the component mounting assembly such that the high dose portion of the x-ray beam strikes the high resolution region, the first low dose portion of the x-ray beam strikes the first low resolution region, and the second low dose portion of the x-ray beam strikes the second low resolution region; and the component mounting assembly is operable to rotate about the object by at least 180 degrees plus the high dose fan angle.

7. A computed tomography scanner as claimed in claim 6 wherein:

the computed tomography scanner further comprises a processor module;

each of the individual detector elements is configured to provide a plurality of signals to the processor module corresponding to the number of x-ray photons detected; and the processor module is configured to receive the signals from the individual detector elements and reconstruct one or more computed tomography images from the received signals.

8. A computed tomography scanner as claimed in claim 1 wherein:

the x-ray beam comprises a single low dose portion and the detector assembly comprises a high resolution region and a single low resolution region;

the high dose portion of the x-ray beam is configured to pass through a high interest region within an object, and the single low dose portion of the x-ray beam is configured to pass through a low interest region within the object;

the detector assembly is positioned on the component mounting assembly such that the high dose portion of the x-ray beam strikes the high resolution region and the single low dose portion of the x-ray beam strikes the single low resolution region; and the component mounting assembly is operable to rotate approximately 360 degrees about the object.

9. A computed tomography scanner as claimed in claim 8 wherein:

the computed tomography scanner further comprises a processor module;

each of the individual detector elements is configured to provide a plurality of signals to the processor module corresponding to the number of x-ray photons detected; and the processor module is configured to receive the signals from the individual detector elements and reconstruct one or more computed tomography images from the received signals.

10. A computed tomography scanner as claimed in claim 1 wherein:

the computed tomography scanner further comprises a base having a pedestal;

the component mounting assembly comprises a rotating plate rotatably coupled to the pedestal and a translating plate moveably coupled to the rotating plate such that the translating plate is moveable in a translating axis; and the translating plate is configured to concurrently translate along the translation axis while the rotating plate rotates about the rotation axis such that the high dose portion of the x-ray beam passes substantially through an eccentrically located high interest region within an object positioned within the path of the x-ray beam.

11. An x-ray filter assembly for use in a computed tomography scanner comprising an x-ray filter and an x-ray shield component, wherein:

the x-ray filter comprises:
a first filter element,
a second filter element,
a filter enclosure defining a recess and a filter lid,
the filter lid is coupled to the filter enclosure and comprises a corresponding opening that is aligned with an opening of the x-ray shield component and a filter opening when the filter lid is coupled to the filter enclosure,
the first and second filter elements are slidably positioned within the recess such that a size of the filter opening is defined by a distance of the first filter element from the second filter element, and
the x-ray shield component is positioned within the recess in a plane in front of or behind the first and second filter elements;

the x-ray shield component comprises an x-ray absorbing material that prevents passage of x-ray photons and defines an opening through which x-ray photons may pass such that the x-ray shield component shapes an x-ray beam comprising the x-ray photons that pass through the opening;

the x-ray filter comprises the filter opening and a filter portion, and is positioned in front of or behind the x-ray shield component along a path of the x-ray beam; and the x-ray filter is configured to allow x-ray photons propagating toward a detector assembly to pass through the filter opening to form a high dose portion of the x-ray beam, and reduce a number of x-ray photons propagating toward the detector assembly through the filter portion to form one or more low dose portions of the x-ray beam.

12. An x-ray filter assembly as claimed in claim 11 wherein the filter opening of the x-ray filter is adjustable to increase and decrease the size of the high dose portion of the x-ray beam.

13. An x-ray filter assembly as claimed in claim 11 wherein:

the first filter element and the second filter element are positioned in a filter plane; and a position of the first filter element and a position of the second filter element is adjustable such that the size of the filter opening and the high dose portion of the x-ray beam is adjustable.

14. A method of generating a computed tomography image of an object comprising:

generating an x-ray beam with an x-ray tube, wherein the x-ray beam comprises a plurality of x-ray photons propagating toward a detector assembly;

filtering the x-ray beam with a filter assembly such that the x-ray beam comprises at least one high dose portion and at least one low dose portion, wherein the high dose portion propagates toward the detector assembly through a high interest region within the object, and the low dose portion has a lower a number of x-ray photons than the high dose portion and propagates toward the detector assembly through a low interest region within the object, the filter assembly comprising:
a first filter element,
a second filter element, a filter enclosure defining a recess and a filter lid, the first and second filter elements are slidably positioned within the recess such that a size of a filter opening is defined by a distance of the first filter element from the second filter element, an x-ray shield component is positioned within the recess in a plane in front of or behind the first and second filter elements, and the filter lid is coupled to the filter enclosure and comprises a corresponding opening that is aligned with an opening of the x-ray shield component and the filter opening when the filter lid is coupled to the filter enclosure;

rotating the x-ray tube and the detector assembly about the object;

detecting x-ray photons of the high dose portion of the x-ray beam in a high resolution region of the detector assembly and detecting x-ray photons of the low dose portion of the x-ray beam in a low resolution region of the detector assembly; and constructing the computed tomography image from the detected x-ray photons of the detector assembly.

15. A method as claimed in claim 14 wherein the method further comprises concurrently translating the x-ray tube and the detector assembly such that the high dose portion of the x-ray beam passes substantially through an eccentrically located high interest region.

16. A method as claimed in claim 14 wherein:

the x-ray beam is filtered such that the at least one low dose region of the x-ray beam comprises a first low dose region and a second low dose region, and the at least one high dose region of the x-ray beam comprises a single high dose region having a fan angle and is located between the first and second low dose regions; and the method further comprises rotating the x-ray tube and the detector assembly about the object by at least 180 degrees plus the high dose fan angle.

17. A method as claimed in claim 14 wherein:

the x-ray beam is filtered such that the at least one low dose region of the x-ray beam comprises a single low dose region and the at least one high dose region of the x-ray beam comprises a single high dose region; and the method further comprises rotating the x-ray tube and the detector assembly approximately 360 degrees about the object.

\* \* \* \* \*